(12) United States Patent
Oliveros

(10) Patent No.: US 12,163,922 B2
(45) Date of Patent: Dec. 10, 2024

(54) METALLIC FLAW DETECTION SYSTEM AND METHOD

(71) Applicant: Lester Guillotte, Humble, TX (US)

(72) Inventor: Enio Oliveros, Montgomery, TX (US)

(73) Assignee: SPScanco LLC, Humble, TX (US)

( * ) Notice: Subject to any disclaimer, the term of this patent is extended or adjusted under 35 U.S.C. 154(b) by 0 days.

(21) Appl. No.: 17/998,286

(22) PCT Filed: Mar. 29, 2022

(86) PCT No.: PCT/US2022/022236
§ 371 (c)(1),
(2) Date: Nov. 9, 2022

(87) PCT Pub. No.: WO2022/212298
PCT Pub. Date: Oct. 6, 2022

(65) Prior Publication Data
US 2023/0324337 A1 Oct. 12, 2023

Related U.S. Application Data

(60) Provisional application No. 63/167,434, filed on Mar. 29, 2021.

(51) Int. Cl.
G01N 27/83 (2006.01)
G01N 33/2045 (2019.01)
(52) U.S. Cl.
CPC .......... *G01N 27/83* (2013.01); *G01N 33/2045* (2019.01)
(58) Field of Classification Search
CPC .... G01N 27/83; G01N 27/87; G01N 33/2045;
G01N 1/00; G01N 3/00; G01N 5/00;
G01N 7/00; G01N 9/00; G01N 11/00;
G01N 13/00; G01N 15/00; G01N 17/00;
G01N 19/00; G01N 21/00; G01N 22/00;
G01N 23/00; G01N 24/00; G01N 25/00;
G01N 27/00; G01N 29/00; G01N 30/00;
G01N 31/00; G01N 33/00; G01N 35/00;
G01N 37/00; G01N 2201/00; G01N
2203/00; G01N 2223/00; G01N 2291/00;
G01N 2333/00; G01N 2400/00; G01N
2405/00; G01N 2407/00; G01N 2410/00;
G01N 2415/00; G01N 2430/00; G01N
2440/00; G01N 2446/00; G01N 2458/00;
(Continued)

(56) References Cited

U.S. PATENT DOCUMENTS

| 5,456,113 A | 10/1995 | Kwun | |
|---|---|---|---|
| 2012/0038357 A1* | 2/2012 | Brandon | G01N 27/82 324/251 |

(Continued)

*Primary Examiner* — Feba Pothen
*Assistant Examiner* — Brent J Andrews
(74) *Attorney, Agent, or Firm* — Matthew J Patterson

(57) ABSTRACT

Apparatus and methods for detecting flaws in objects comprised of ferromagnetic materials are disclosed. A wireless energizing unit is disclosed that includes an array of permanent magnets is used to induce a magnetic field into the objects and transducers are configured to detect a magnetic flux property in the presence of a flaw in the object. Embodiments that are configured to be clamped over the object are also disclosed. In addition, methods for retrofitting EMI detection systems with a wireless energizing unit are disclosed.

37 Claims, 8 Drawing Sheets

(58) Field of Classification Search
CPC ........... G01N 2469/00; G01N 2470/00; G01N 2474/00; G01N 2496/00; G01N 2500/00; G01N 2510/00; G01N 2520/00; G01N 2550/00; G01N 2560/00; G01N 2570/00; G01N 2600/00; G01N 2610/00; G01N 2650/00; G01N 2800/00
See application file for complete search history.

(56) References Cited

U.S. PATENT DOCUMENTS

2020/0072926 A1     3/2020   Vogel
2020/0379068 A1*   12/2020   Vogel ................... G01R 33/445

* cited by examiner

METALLIC FLAW DETECTION SYSTEM AND METHOD

CROSS REFERENCE TO RELATED APPLICATIONS

This application claims the benefit of U.S. Provisional Application Ser. No. 63/167,434 filed 29 Mar. 2021 as well as Patent Cooperation Treaty Patent Application Serial No. PCT/US 22/22236 filed 29 Mar. 2022. The disclosure of the applications above are incorporated herein by reference in their entirety.

BACKGROUND OF THE DISCLOSURE

Field of the Disclosure

Embodiments of the disclosure generally relates to the field of instrumentation and inspection, more specifically, an apparatus and methods for detecting flaws in metallic structures such as rods, pipes and cables that is not elsewhere provided for.

Description of the Related Art

There exists many apparatuses and methods in the prior art to inspect and detect flaws in ferromagnetic objects. Magnetic nondestructive testing methods are widely used in the world of oil and gas and drill pipe inspection. Magnetic inspection is used to detect a myriad of defects within ferrous pipe and rod. Electromagnetic inspection (EMI) methods are some of the most common testing methods found in the oil and gas industry. Prior art EMI use externally powered magnetizing coils to induce a magnetic field into the rod or pipe. Prior art methods for quantifying a magnetizing coil's "strength" typically use "ampere-turns" as a strength unit of measurement. Ampere-turns is the amount of DC amperes from an external power source flowing through the magnetizing coil multiplied by the number of turns of magnet wire on the magnetizing coil. Because magnetizing coils of the prior art are comprised of solid rings they must be used starting at an end of the piece to be inspected with the end inserted into the middle of the coil. This limits prior art EMI machines' ability to be used for inspection portions of rod or pipe or captured areas of cables (on a bridge for example). Among the other drawbacks of externally powered magnetizing coils of the prior art is that they require power cables and a large power source along with adequate power control making them difficult to transport and use in the field.

What is needed is an EMI inspection method and apparatus that overcomes the problems in the prior art.

SUMMARY OF THE INVENTION

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a magnetic inspection system having a sensor unit that may include at least one wireless energizing unit configured to produce a planar magnetic field in a part of interest where the part of interest is at least in part may include of a ferromagnetic material, and at least one transducer configured to detect a magnetic parameter in the part of interest and produce a magnetic parameter signal. The system also includes a processing unit configured to process the magnetic parameter signal and to output information related to the magnetic parameter. Other embodiments of this aspect include corresponding computer systems, apparatus, and computer programs recorded on one or more computer storage devices, each configured to perform the actions of the methods.

Implementations may include one or more of the following features. The magnetic inspection system where each of the at least one wireless energizing unit may include a ring having an inside diameter and an outside diameter and a bore defined by the inside diameter, and a plurality of permanent magnets circumferentially spaced around the ring between the inside diameter and the outside diameter where each of the plurality of permanent magnets is oriented such that the magnetic field of each of the permanent magnets is directed in a predetermined direction. Each of the at least one wireless energizing unit is positioned at a predetermined angle relative to the part of interest. The predetermined angle is between substantially 1 degree and 90 degrees relative to the part of interest. The plurality of permanent magnets circumferentially spaced around the ring may include a Halbach array having a magnetization pattern of any of k=2, k=3 and k=4. The Halbach array is of a type k=2 and the planar magnetic field is in accordance with the following $H=Mr \ln(Ro/Ri)y$ where Mr is a ferromagnetic remanence, Ri is the inside radius of the ring and Ro is the outside radius of the ring and a direction of the planar magnetic field is y. The magnetic parameter is any of a magnetic flux, a magnetic flux density and a magnetic flux leakage. The magnetic flux leakage is used to determine a flaw in the part of interest and the magnetic parameter signal is a flaw detection signal. The at least one wireless energizing unit may include a first wireless energizing unit and a second wireless energizing unit. The first wireless energizing unit is configured to produce the planar magnetic field in a first planar magnetic field direction and the second wireless energizing unit is configured to produce the planar magnetic field in a second planar magnetic field direction. The first planar magnetic field direction can be substantially equal to the second planar magnetic field direction. The first planar magnetic field direction can be substantially different from the second planar magnetic field direction. The first wireless energizing unit the second wireless energizing unit are configured to rotate independently of one another. The ring is may include a first ring portion and a second ring portion, and where the first ring portion is fixedly attached to the first chassis half and the second ring portion is fixedly attached to the second chassis half and where the first chassis half and the second chassis half are positioned over the part of interest and removably coupled together joining the first ring portion and the second ring portion slidably capturing the part of interest in the bore formed therebetween. The magnetic inspection system is configured to permit the part of interest to be translated along a linear length of the part of interest. The linear measurement device is configured to indicate a position of the flaw along the linear length of the part of interest when the at least one transducer detects the magnetic flux leakage. The magnetic inspection system may include a first V-groove wheel rotatably fixedly attached to the first chassis half and a second V-groove wheel rotatably fixedly attached to the second chassis half and configured to engage with the part of interest and position the part of interest proximate the center of the bore of the ring. The ring, the first chassis half, and the second chassis half are comprised of a non-ferromagnetic material. The first V-groove wheel and the second V-groove wheel are comprised of a non-ferromagnetic material. The part of interest may include a circular cross section, a linear length and a centerline through the circular cross section along the linear length, and the part of interest is configured to be positioned within the bore and the ring of the at least one wireless energizing unit is configured to be positioned at a predetermined angle to the centerline and configured to induce the planar magnetic field in the part of interest with the direction of the planar magnetic field along at least a portion of the linear length. The at least one wireless energizing unit is configured to be positioned at different locations along the linear length of the part of interest. The ring may also be configured to rotate about the centerline and further configured to rotate about the center of the diameter of the ring. Implementations of the described techniques may include hardware, a method or process, or computer software on a computer-accessible medium.

One general aspect includes an energizing unit for use with an inspection unit a wireless energizing unit configured to produce a planar magnetic field in a part of interest where the part of interest is at least in part may include of a ferromagnetic material, the wireless energizing unit may include a ring having an inside diameter and an outside diameter and a bore defined by the inside diameter, and a plurality of permanent magnets circumferentially spaced around the ring between the inside diameter and the outside diameter where each of the plurality of permanent magnets is oriented such that the magnetic field of each of the permanent magnets is directed in a predetermined direction. Other embodiments of this aspect include corresponding computer systems, apparatus, and computer programs recorded on one or more computer storage devices, each configured to perform the actions of the methods.

Implementations may include one or more of the following features. The energizing unit where the plurality of permanent magnets circumferentially spaced around the ring may include a Halbach array having a magnetization pattern of any of k=2, k=3 and k=4. The Halbach array is of a type k=2 and the planar magnetic field is in accordance with the following: H=Mr ln(Ro/Ri)y where Mr is a ferromagnetic remanence, Ri is the inside radius of the ring and Ro is the outside radius of the ring and a direction of the planar magnetic field is y. The ring may include a first ring portion and a second ring portion, and where the first ring portion and the second ring portion are positioned over the part of interest and removably coupled together joining the first ring portion and the second ring portion slidably capturing the part of interest in the bore formed therebetween. The wireless energizing unit can be retrofit to an EMI inspection unit. Implementations of the described techniques may include hardware, a method or process, or computer software on a computer-accessible medium.

One general aspect includes a method of inspecting a ferromagnetic part of interest. The method also includes producing at least one planar magnetic field in the part of interest using at least one wireless energizing unit, and detecting a magnetic parameter using at least one transducer, producing a magnetic parameter signal, and outputting information related to the magnetic parameter using a processing unit. Other embodiments of this aspect include corresponding computer systems, apparatus, and computer programs recorded on one or more computer storage devices, each configured to perform the actions of the methods.

Implementations may include one or more of the following features. The method of inspecting a ferromagnetic part of interest where each of the at least one wireless energizing unit may include a ring having an inside diameter and an outside diameter and a bore defined by the inside diameter, and a plurality of permanent magnets circumferentially spaced around the ring between the inside diameter and the outside diameter where each of the plurality of permanent magnets is oriented such that the magnetic field of each of the permanent magnets is directed in a predetermined direction. The method of inspecting a ferromagnetic part of interest may include positioning the part of interest within the bore of the at least one wireless energizing unit and positioning of the at least one wireless energizing unit at a predetermined angle relative to the part of interest. The predetermined angle is between substantially 1 degree and 90 degrees relative to the part of interest. The plurality of permanent magnets circumferentially spaced around the ring may include a Halbach array having a magnetization pattern of any of k=2, k=3 and k=4. The Halbach array is of a type k=2 and producing the planar magnetic field is in accordance with the following: H=Mr ln(Ro/Ri)y where Mr is a ferromagnetic remanence, Ri is the inside radius of the ring and Ro is the outside radius of the ring and a direction of the planar magnetic field is y. The detecting the magnetic parameter is any of detecting a magnetic flux, detecting a magnetic flux density and detecting a magnetic flux leakage. The method of inspecting a ferromagnetic part of interest determining a flaw in the part of interest the magnetic flux leakage is detected and producing a flaw detection signal. The at least one wireless energizing unit may include a first wireless energizing unit and a second wireless energizing unit. The method of inspecting a ferromagnetic part of interest may include producing the planar magnetic field in a first planar magnetic field direction using the first wireless energizing unit and producing the planar magnetic field in a second planar magnetic field direction using the second wireless energizing unit. The first planar magnetic field direction can be substantially equal to the second planar magnetic field direction. The first planar magnetic field direction can be substantially different from the second planar magnetic field direction. The method of inspecting a ferromagnetic part of interest may include rotating the first wireless energizing unit about the part of interest and rotating the second wireless energizing unit about the part of interest. The ring may include a first ring portion and a second ring portion, the method may include positioning the first ring portion and the second ring portion over the part of interest, attaching the first ring portion to a first chassis half, attaching the second ring portion to a second chassis half, coupling the first chassis half and the second chassis together, and slidably capturing the part of interest in the bore formed the first ring portion and the second ring portion. The method of inspecting a ferromagnetic part of interest may include translating the part of interest along a linear length and measuring a linear distance of translation. The method of inspecting a ferromagnetic part of interest may include indicating a position of the flaw along the linear length of the part of interest when the flaw detection signal is produced. The method of inspecting a ferromagnetic part of interest may include centering the part of interest in the bore of the ring. The method of inspecting a ferromagnetic part of interest may include selecting a non-ferromagnetic material to comprise the ring, the first chassis half and the second chassis half. The part of interest may include a circular cross section, a linear length and a centerline through the circular cross section along the linear length, and the method may include positioning the at least one wireless energizing unit at a predetermined angle to the part of interest may include positioning the at least one wireless energizing unit at a predetermined angle to at a predetermined angle to the centerline, and producing at least one planar magnetic field in the part of interest may include producing the planar magnetic field in the part of interest with the direction of the planar magnetic field along at least a portion of the linear length. The method of inspecting a ferromagnetic part of interest further may include positioning the at least one wireless energizing unit at different locations along the linear length of the part of interest. The method of inspecting a ferromagnetic part of interest may include rotating the ring about the centerline. Implementations of the described techniques may include hardware, a method or process, or computer software on a computer-accessible medium.

One general aspect includes a method of producing a magnetic field in a part of interest includes producing at least one planar magnetic field in the part of interest using at least one wireless energizing unit where the at least one wireless energizing unit may include a ring having an inside diameter and an outside diameter and a bore defined by the inside diameter, and a plurality of permanent magnets circumferentially spaced around the ring between the inside diameter and the outside diameter where each of the plurality of permanent magnets is oriented such that the magnetic field of each of the permanent magnets is directed in a predetermined direction. The method also includes positioning the part of interest within the bore. Other embodiments of this aspect include corresponding computer systems, apparatus, and computer programs recorded on one or more computer storage devices, each configured to perform the actions of the methods.

Implementations may include one or more of the following features. The method of producing a magnetic field in a part of interest where the plurality of permanent magnets circumferentially spaced around the ring may include a Halbach array having a magnetization pattern of any of k=2, k=3 and k=4. The Halbach array is of a type k=2 and producing the at least one planar magnetic field is in accordance with the following: H=Mr ln(RoRi)y where Mr is a ferromagnetic remanence, Ri is the inside radius of the ring and Ro is the outside radius of the ring and a direction of the planar magnetic field is y. The ring may be comprised of a first ring portion and a second ring portion, the method may include positioning the first ring portion and the second ring portion over the part of interest and removably coupling the first ring portion and the second ring portion together and slidably capturing the part of interest in the bore formed between the first ring portion and the second ring portion. Implementations of the described techniques may include hardware, a method or process, or computer software on a computer-accessible medium.

One general aspect includes a method of retrofitting an EMI inspection unit. The method also includes removing the powered magnetizing coil, and adding a wireless energizing unit, the wireless energizing unit may include a ring having an inside diameter and an outside diameter and a bore defined by the inside diameter, and a plurality of permanent magnets circumferentially spaced around the ring between the inside diameter and the outside diameter where each of the plurality of permanent magnets is oriented such that the magnetic field of each of the permanent magnets is directed in a predetermined direction. Other embodiments of this aspect include corresponding computer systems, apparatus, and computer programs recorded on one or more computer storage devices, each configured to perform the actions of the methods.

Implementations may include one or more of the following features. The method of retrofitting an EMI inspection unit where the plurality of permanent magnets circumferentially spaced around the ring may include a Halbach array having a magnetization pattern of any of k=2, k=3 and k=4. The Halbach array is of a type k=2 and producing a planar magnetic field is in accordance with the following: H=Mr ln(RoRi)y where Mr is a ferromagnetic remanence, Ri is the inside radius of the ring and Ro is the outside radius of the ring and a direction of the planar magnetic field is y. The ring may be comprised of a first ring portion and a second ring portion, and where the first ring portion and the second ring portion are positioned over a part of interest and removably coupled together joining the first ring portion and the second ring portion slidably capturing the part of interest in the bore formed therebetween. Implementations of the described techniques may include hardware, a method or process, or computer software on a computer-accessible medium.

BRIEF DESCRIPTION OF THE DRAWINGS

So that the manner in which the above-recited features of the present disclosure can be understood in detail, a more particular description of the disclosure, briefly summarized above, can be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein can be practiced. It is to be understood that other embodiments can be utilized, and structural changes can be made without departing from the scope of the disclosure.

All of the methods disclosed and claimed herein can be made and executed without undue experimentation in light of the present disclosure. While the apparatus and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the disclosure.

Although the invention(s) is/are described herein with reference to specific embodiments, various modifications and changes can be made without departing from the scope of the present invention(s), as presently set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Figure 1:
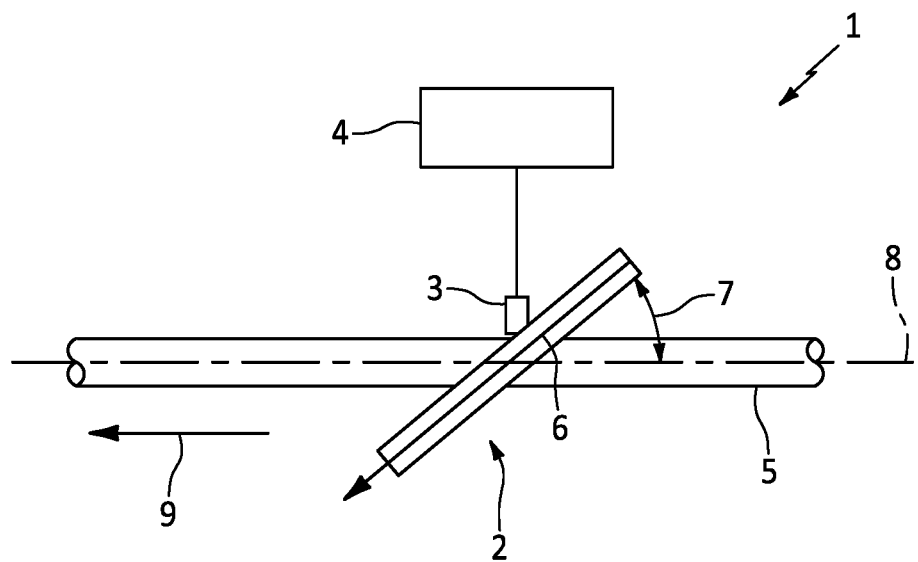
FIG. 1 is a conceptual diagram of a top view of an inspection system in accordance with the present disclosure.

Referring first to FIG. 1, there is shown is a highly conceptualized illustration that will be used to illustrate the basic components and operational principals of an magnetic inspection system 1 of the present disclosure. Magnetic inspection system 1 is comprised of an wireless energizing unit 2, a transducer 3 and a processing unit 4. Wireless energizing unit 2 produces a magnetic field 6 in the direction of the arrow (moving from negative to positive). The magnetic field 6 is imparted into a ferromagnetic part. In the embodiment shown, the ferromagnetic part can have any cross sectional shape such as a rod 5 having a circular cross section. The magnetic field is inventively produced within rod 5 in the plane of wireless energizing unit 2 as will disclosed in more detail herein after. Magnetic field 6 is uniformly produced in a ferromagnetic material wherein the material is contiguous, however when it is not, as in the case of flaw (groove, gouge, ring, pit, crack, gap, broken strand, etc.), a magnetic flux leakage is produced. Transducer 3 is configured to detect a magnetic parameter such magnetic flux fields and is further configured to send a magnetic parameter signal to processing unit 4. Transducer 3 can comprise one or more Hall effect transducers and/or one or more search coils that are positioned in the immediate vicinity of the rod 5. Flaw detection signals, in the form of responses of the transducer are used to measure flux leakage or magnetic flux density. Transducer 3 can comprise any known type of transducer configured to detect and measure a magnetic flux property such as flux leakage and magnetic flux density including Hall effect sensors and search coil magnetometer and the like. These measurements are, in turn, used to detect and to quantify localized flaws in the rod such as grooves, gouges, pits and the like. The transducer responses are output to the processing unit 4. Processing unit 4 includes hardware and software configured to process the signal from transducer 3, along with other sensor input, to output information to indicate the position, type and size of a flaw as will be disclosed in more detail herein after. It should be apparent to those skilled in the art that as rod 5 is translated in direction 9 relative to magnetic inspection system 1 a predetermined linear length of the rod can be inspected. In certain embodiments of the present disclosure rod 5 is translated linearly to inspect different locations and magnetic inspection system 1 remains stationary and in other embodiments the inspection system is configured to be translated and the rod (or other ferromagnetic material of interest) remains stationary. In other embodiments wireless energizing unit 2 can be rotated about the centerline 8 of the rod 5. It should be noted to those skilled in the art that it has been discovered that wireless energizing unit 2 positioned at an angle 7, relative to centerline 8 of rod 5, produces a planar magnetic field that when interrupted by a flaw can produce detectable and repeatable signals by transducer 3 as will be disclosed in more detail herein after.

Figure 2:
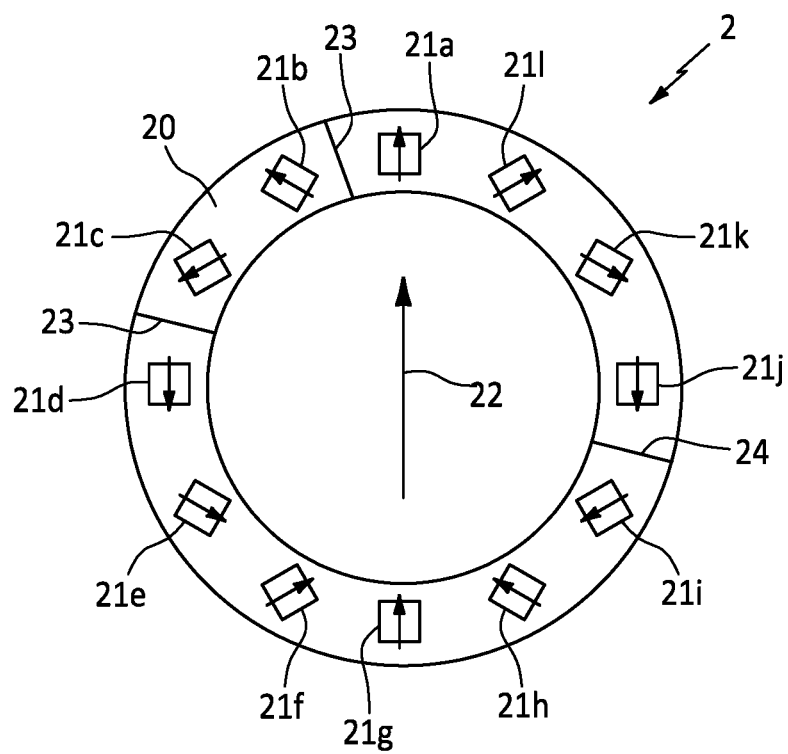
FIG. 2 is a side view of an energizing unit in accordance with the present disclosure.

Referring now to FIG. 2, there is shown an embodiment of wireless energizing unit 2 in more detail comprising ring 20 and permanent magnets 21a-21l arranged evenly circumferentially spaced around midpoint circumference of the ring between its inside diameter and outside diameter. In some embodiments, ring 20 is elliptical (or other outer shapes) and in these particular embodiments the magnets are spaced around an outer periphery but may not necessarily be evenly spaced. With the permanent magnets circumferentially spaced, the magnets 21a-21l can comprise any type of permanent magnet or electromagnetic magnets and can comprise rare earth magnets. The direction of the magnetic field for each of the magnets 21a-21l is indicated by the arrow for each of the respective magnets. Although the embodiment in FIG. 2 comprises 12 magnets 21a-21l, embodiments with more or fewer magnets are contemplated to be within the scope of the present disclosure as will be disclosed herein after. Ring 20 is comprised of a non-ferromagnetic material and which material can include plastics, aluminum, some stainless steels and the like. It should be appreciated by those skilled in the art that ring 20 can comprise other shapes, such as elliptical, depending on the shape of the magnetic field desired and the object to be inspected. As will be discussed in more detail herein after, ring 20 can be configured to produce different magnetic fields and magnetization patterns such as those produced by a Halbach array of k=2, k=3 and k=4 or combinations thereof. In addition, a plurality of rings 20 can be used and which plurality of rings can be oriented at the same predetermined angle 7 relative to the centerline 8 (FIG. 1) or at differing predetermined angles. In addition to ring 20 being positioned at a different predetermined angle 7, ring 20 can be rotated around centerline 8 to detect specific flaws or general types of flaws in rod 5. Ring 20 can also be configured to rotate about the centerline of its diameter to reposition the planar magnetic field relative to the orientation of the rod 5. Ring 20 further can include pockets formed or machined therein to receive magnets 21a-21l therein and the magnets may be affixed therein using any known techniques. In some embodiments, magnets 21a-21l are press fit into the pockets in ring 20 and can be affixed using an appropriate adhesive. In some embodiments of the present disclosure, magnets 21a-21l are approximately 0.63-inch cubes and are comprised of neodymium type of magnet although other sizes and types of magnets are within the scope the present disclosure. It should be appreciated by those skilled in the art that the size and type of the magnets affect the size and strength of the magnetic field 22 (6 in FIG. 1) produced by wireless energizing unit 2. For instance, larger magnets can be used to produce a larger magnetic field for larger objects. The increase in the size and/or width of the magnets can increase the width of the magnetic field produced. In the embodiment shown, magnets 21a-21l produce a combined magnetic field in the plane of ring 2 and in the direction of arrow 6. It should be appreciated by those skilled in the art that wireless energizing unit 2 resembles a Halbach array of the type k=2. For the special case of an Halbach array wherein k=2, the magnetic field 22 inside the bore is uniform and is given by $$H = M_r \ln\left(\frac{R_o}{R_i}\right) \hat{y} \qquad \text{(Equation 1)}$$

where $M_r$ is the ferromagnetic remanence, and the inner radius and outer radius of ring 20 are $R_i$ and $R_o$ respectively. The magnetic field H is in the y direction (direction of arrow 22). In certain embodiments for detecting flaws in an object having a diameter between 0.75 inches and 1.13 inches $R_i$ can be approximately 6 inches and $R_o$ can be approximately 8 inches. Ring 20 further includes split lines 23, 24 splitting the ring into a first portion and a second portion which allows the ring to be opened such that wireless energizing unit 2 can be installed over an object of interest even if that object is captured between other pieces such that there is no free end. Examples include cables on a bridge, connected tubulars and continuous rod sections in the oil and gas a-industry and the like. The split ring can include alignment features, hinges and closure devices as are known in the art (not shown).

Figure 3:
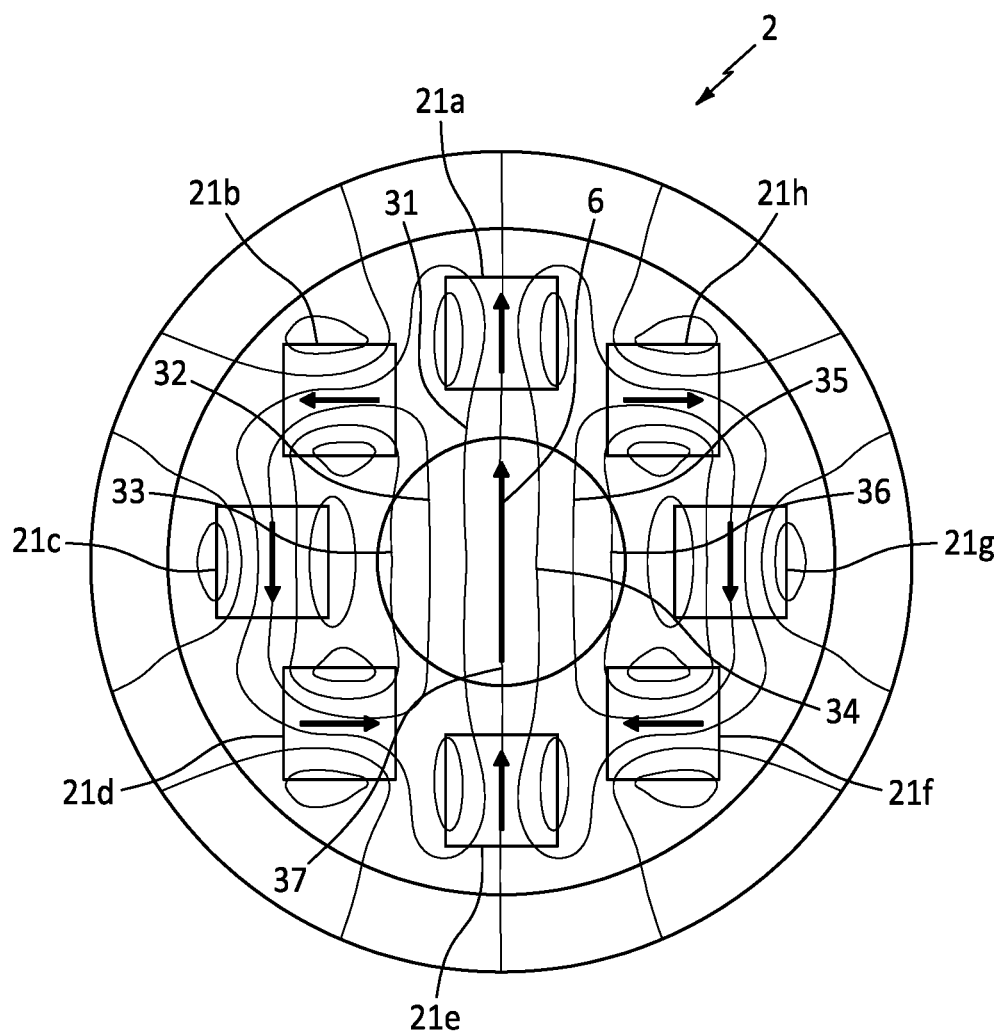
FIG. 3 is a conceptual diagram of the magnetic fields produced by an energizing unit accordance with the present disclosure.

The magnetic fields produced by the individual magnets and the combined magnetic effect can best be visualized with reference to FIG. 3. The embodiment shown includes 8 magnets 21a-21h and the direction of the magnetic field for each of the magnets is indicated by the arrow for each of the respective magnets. It can be seen that magnets 21a-21e produce a combined magnetic field 31 and that magnets 21b-21d produced combined magnetic fields 32, 33. magnets 21a-21e produce a combined magnetic field 31 and that magnets 21b-21d produced combined magnetic fields 32, 33. Similarly, magnets 21a and 21e-21h produce a combined magnetic field 34 and that magnets 21f-21h produced combined magnetic fields 35, 36. Further magnets 21a, 21e produce combined magnetic field 37. Because of the orientation of magnets 21a-21h, the combined magnetic fields 31-37 produce a total combined planar (with respect to the plane of ring 20) magnetic field in the direction of arrow 6.

Figure 4:
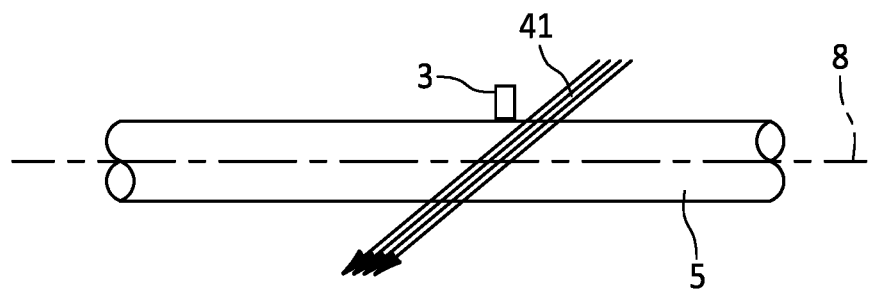
FIG. 4 is a diagrammatic view of the combined magnetic field in accordance with the present disclosure.
Figure 5:
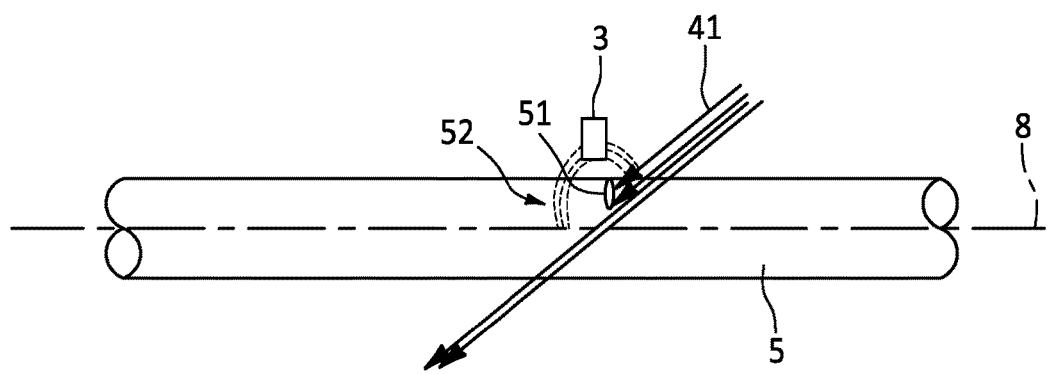
FIG. 5 is a diagrammatic view of a magnetic flux leak associated with a flaw in accordance with the present disclosure.

Referring to FIG. 4, there is shown a schematic representation of combined magnetic fields 41 produced by wireless energizing unit 2 in the direction of the arrows through rod 5. It should be appreciated that wireless energizing unit 2 produces a magnetic field both in the longitudinal direction of rod 5 in the direction of centerline 8 as well as in direction transverse to the centerline. In this particular figure, rod 5 is free of flaws or imperfections and the combined magnetic field is established in the rod and no magnetic flux leakage (MFL) or change in magnetic flux density are detected at transducer 3. Now with reference to FIG. 5, there is show rod 5 with a flaw 51 positioned within the rod such that it disrupts part of the combined planar magnetic field 41 in the direction of the arrows (the planar magnetic field direction). The portion of combined magnetic field 41 that is disrupted leaks out of rod 5 and produces MFL 52. Transducer 3 is positioned and configured to detect MFL 52. As will be disclosed in more detail hereinafter, magnetic inspection system 1 can include other equipment and sensors that communicate with processor 4 (FIG. 1) to enable the type, depth and position of a flaw to be discovered.

Figure 6:
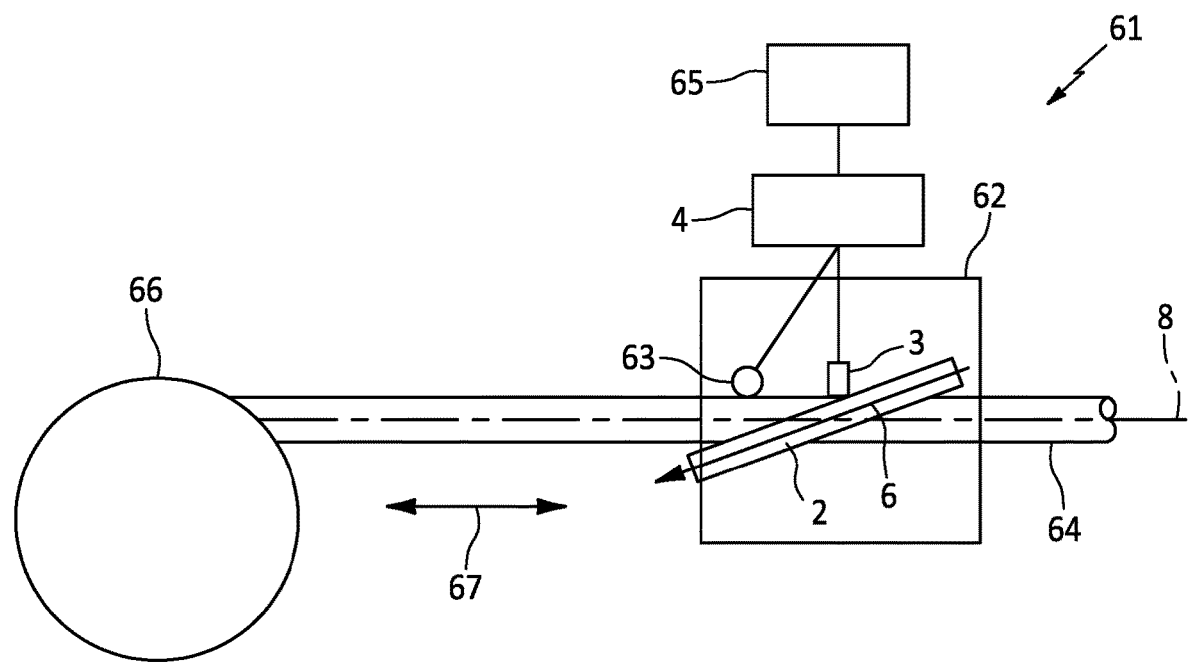
FIG. 6 is a diagrammatic view of an embodiment a flaw detection system in accordance with the present disclosure.

One embodiment of an inspection system 61 of the present disclosure in operation can be seen with reference to FIG. 6. In this particular example, inspection system 61 is positioned to inspect a continuous rod string 64 as can be typically found in the oil and gas industry. Still referring to FIG. 6, the continuous rod string 64 is passed through a sensor unit 62. Sensor unit 62 includes wireless energizing unit 2 and transducer 3 disclosed herein above as well as linear measurement device 63. In some embodiments, energizing unit can be opened up along cut lines 23, 24 (FIG. 2) and advantageously placed over continuous rod string 64 without having to start at an end of the continuous rod string. Sensor unit 62 can be positioned between the well head and the injector, between the injector and a rod guiding element in the mast (all not shown), or at the end of the guiding element prior to coiling the rod into a service or transport reel. Linear measurement device 63 is used to measure the linear distance of translation in determining the length increment of continuous rod string 64 within the sensor unit 62 with respect to a reference point on the continuous rod string. As an example, the reference point can be the downhole end of the continuous rod string. Length measurement signals from linear measurement device 63 and MFL detection signals from transducer 3 are responses generated by the sensor unit 62 and are connected to processing unit 4. The output of the linear measurement device 63 is also input to the processing unit 4. The processing unit 4 generates a record of cross sectional area and flaws in the continuous rod string 64, as will be discussed in detail in subsequent sections of this disclosure. Processing unit 4 can include a recorder, a memory device or other output device configured to produce a record of the inspection process. The record is preferably a "log" of these data with respect to distance along the continuous rod string 64. The log of these data is preferably generated in real time and can be generated by means cooperating with the processing unit 4 by means of wired or wireless communication. The data can also be gathered and processed, and a report is produced to summarize the rod condition.

Processing unit 4 can also be operatively connected to a display 65 which presents an operator of the inspection system 61 with a "live" display of continuous rod condition as it is translated through sensor unit 62. The processing unit 4 is also operationally connected to drive 66 which operates to translate continuous rod string 64 through sensing unit 62 of the inspection system 61 in either predetermined direction indicated by arrow 67. If continuous rod conditions, such as detected flaws, as determined by computations within the processing unit 4, exceed a predetermine standard, the processing unit can stop continuous rod conveyance within the sensing unit 62 by disabling the drive unit 66. This step can alternately be performed manually by the inspection system operator based upon information from the display 65.

The generated log (e.g., a hard copy record) typically indicates the time of each measured flaw, the position and length dimensions of the flaw relative to a reference point such as the downhole end of the continuous rod 64, and the direction of rod movement 67 when sampling occurs. The inspection system 61 can also provide a real-time two dimensional display of the continuous rod at 65, or alternately continuous rod cross sectional area as a function of linear length positioned at different locations along the string.

Figure 7:
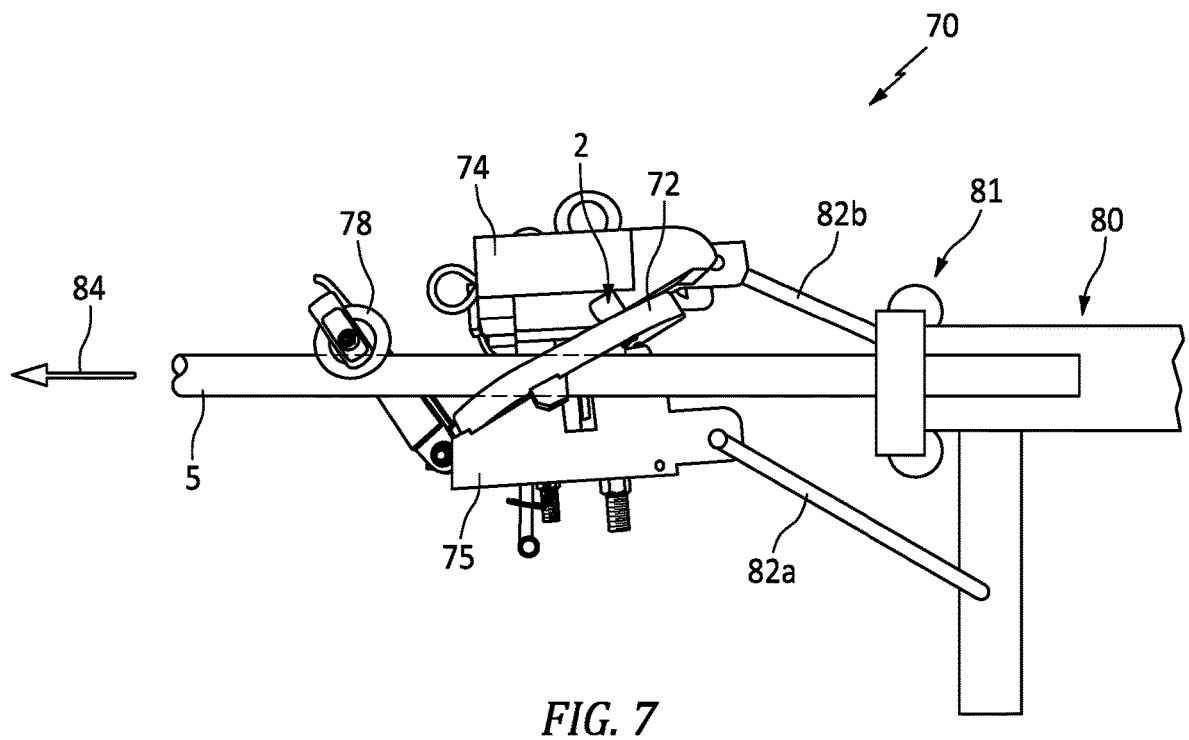
FIG. 7 is a side view of an embodiment of a flaw detection system in accordance with the present disclosure.
Figure 8:
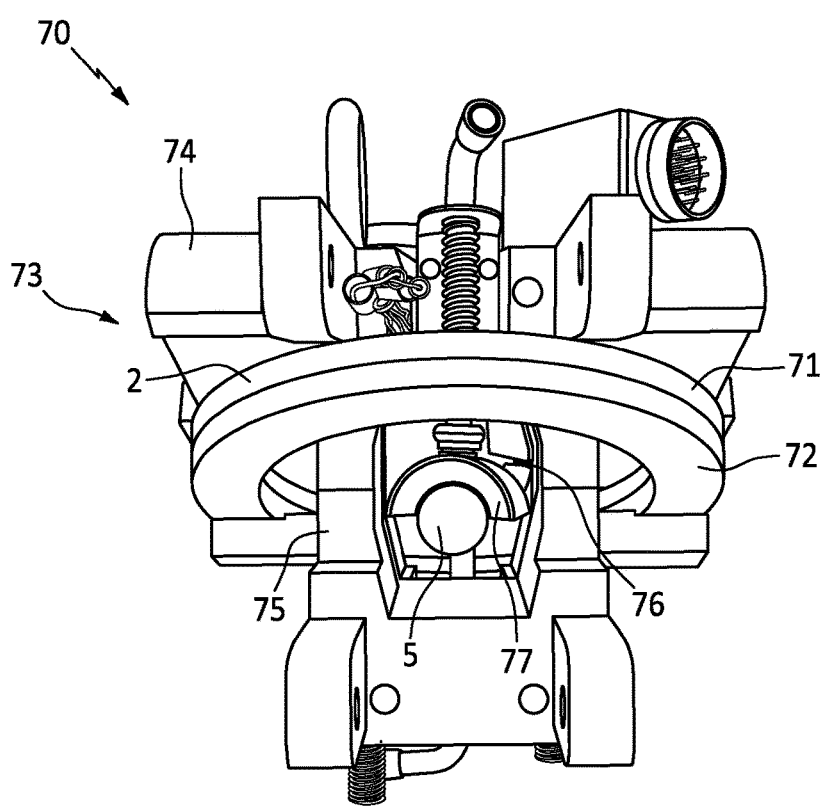
FIG. 8 is an end view of an embodiment of a flaw detection system in accordance with the present disclosure.

Referring next to FIGS. 7 and 8 there is shown an embodiment of inspection system 70 incorporating the principles disclosed in the present disclosure herein above that is configured to be positioned over a part to be inspected, such as rod 5. Inspection system 70 includes wireless energizing unit 2 having a first ring portion 71 and a second ring portion 72 having a plurality of magnets arranged therein in a Halbach array as described herein above. Inspection system 70 further includes chassis 73 comprised of a first chassis half 74 and a second chassis half 75 wherein first ring portion 71 is removably fixedly attached to the first chassis half and second ring portion 72 is removably fixedly attached to the second chassis half. The first chassis half 74 and the second chassis half 75 are removably fixedly attached to each other using fasteners as will be described in more detail herein after. Inspection system 70 further includes a plurality of transducers wherein the plurality of transducers can comprise Hall effect transducers and can include more or fewer transducers. First magnetic flux leakage sensor assembly 76 is shown mounted to first chassis half 74 and includes first transducer 77 mounted to a spring assembly to bias the transducer in a downward direction to maintain contact with rod 5 during the inspection process as will be described in more detail herein after. It should be noted that certain embodiments include four transducers positioned to monitor four planes around the circumference of rod 5 to detect magnetic flux leakage if a flaw is present with in the rod. Also included in the embodiment is V-groove wheel 78 wherein V-groove wheel 78 is mounted to second chassis half 75. Also shown in the figures is rod support 80 that includes guide assembly 81 for supporting rod 5 as is known in the industry. Inspection system 70 further includes support assembly 82*a*, 82*b* removably attached second chassis half 75 and to rod support 80 to prevent movement and rotation of the inspection system as will be described in more detail hereinafter. The various components of inspection system 70 can be comprised of any of variety of non-ferromagnetic materials including plastics, aluminum, some stainless steels and the like.

Figure 9:
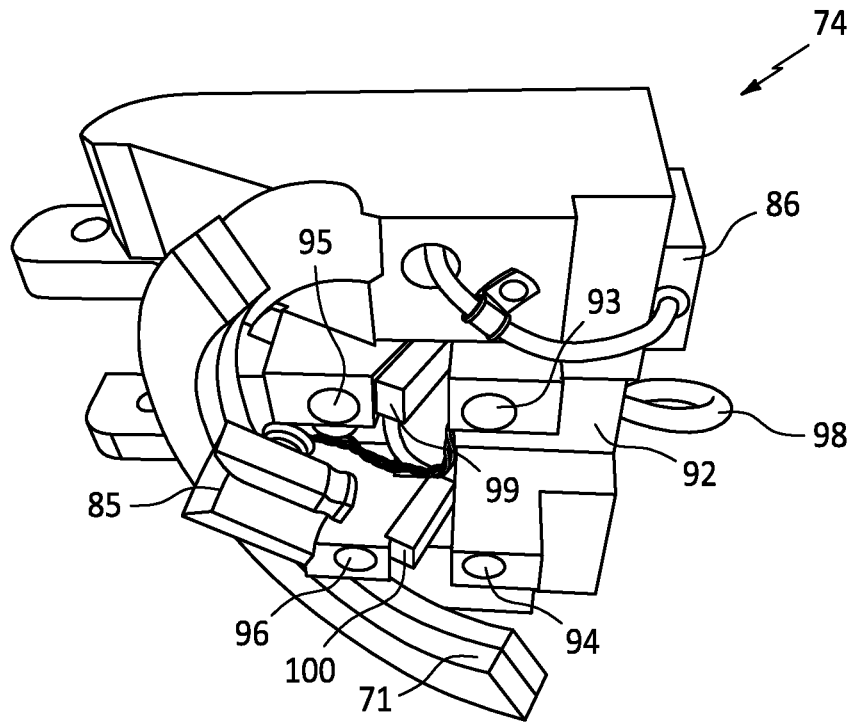
FIG. 9 is a bottom view of an embodiment of a chassis of a flaw detection system in accordance with the present disclosure.
Figure 10:
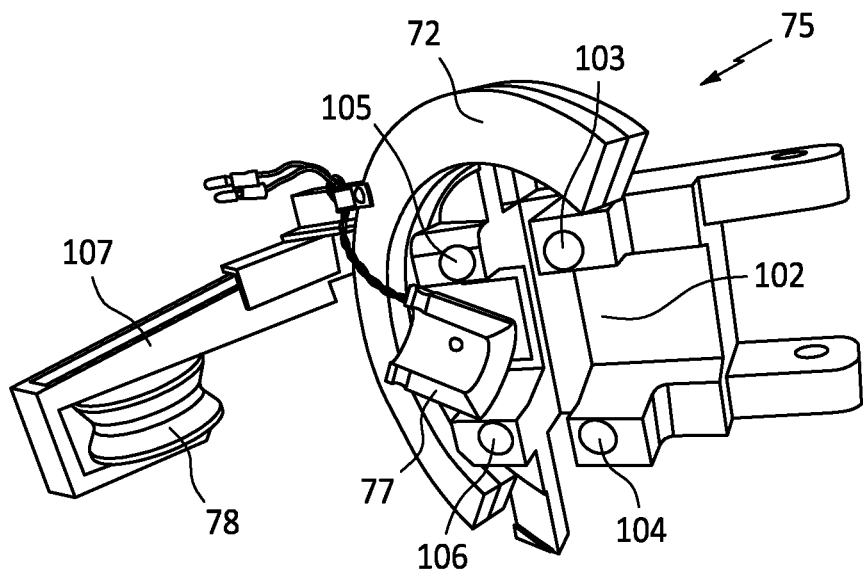
FIG. 10 is a top view of an embodiment of a chassis of a flaw detection system in accordance with the present disclosure.

Now referring to FIGS. 9, 10 there is shown the inside detail of first chassis half 74 and second chassis half 75 respectively and the mating surfaces and features there between. With reference to FIG. 9, first chassis half 74, is configured to secure first ring portion 71 thereto. First chassis half 74 further includes first half channel 92, and alignment bores 93, 94, 95, 96 positioned therein. Also shown is second transducer 85 and accelerometer 86. Second transducer 85 is similar to first transducer 77 and is part of second magnetic flux leakage sensor assembly including a spring assembly to bias the transducer in an upward direction to maintain contact with rod 5 during the inspection process as will be described in more detail herein after. Accelerometer 86 is configured to provide acceleration information to processing unit 4 (FIG. 1) concerning the vibration in magnetic inspection system 1 to remove noise induced into the system from sudden movements of the rod 5 or other excessive vibration events. Also shown is lifting eye 98 mounted to first chassis half to facilitate the lifting and aligning of inspection system 70 during use. First magnetic flux density sensor 99 and second magnetic flux density sensor 100 are mounted to first half chassis 74 to position the magnetic flux density sensors proximate rod 5 during use. It should be appreciated by those skilled in the art that by monitoring the magnetic flux density, inspection system 70 can determine changes in the cross section of rod 5, reductions in the outside diameter of the rod i.e. from wear), changes in permeability and other flaws.

Now with reference to FIG. 10, second chassis half 75, is configured to secure second ring portion 72 thereto. Second chassis half 75 further includes second half channel 102, alignment pins 103, 104,105, 106 positioned thereon. Also shown is V-groove wheel 78 mounted to second chassis half by support 107. In operation, first chassis half 74 and second chassis half 75 are assembled, with alignment pins 103, 104,105, 106 mating alignment bores 93, 94, 95, 96 respectively. It should be appreciated by those skilled in the art that in so assembling first chassis half 74 and second chassis half 75 first half channel 92 and second half channel 102 are aligned to create a full channel wherein the full channel is sized to accommodate and align rod 5 therein for inspection using inspection 70. It should be further appreciated that have mounting surfaces positioned a predetermined angle relative to first chassis half 74 and second chassis half 75 such that when assembled first ring portion 71 and second ring portion 72 create a full ring positioned at the predetermined angle relative to rod 5 as disclosed with respect to the various figures disclosed herein above. For example, in an embodiment wherein the diameter of rod 5 is 1 inch in diameter, the predetermined angle 7 (FIG. 1) can be as close to 0 degrees as practicable and as much as 90 degrees relative to the centerline 8 (FIG. 1) of the rod.

Figure 11:
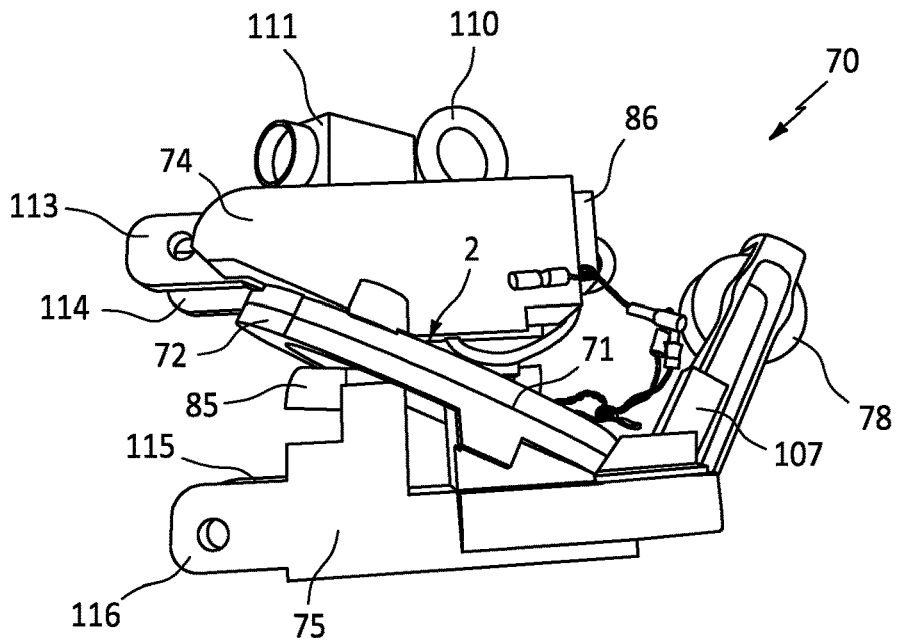
FIG. 11 is a side view of an embodiment of a chassis of a flaw detection system in accordance with the present disclosure.
Figure 12:
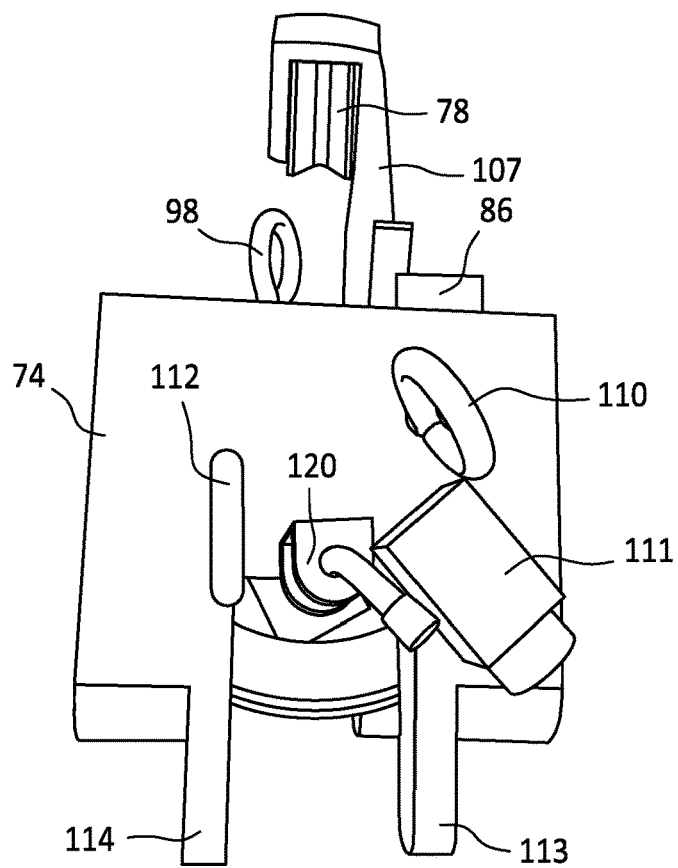
FIG. 12 is a top view of an embodiment of a chassis of a flaw detection system in accordance with the present disclosure.

Now referring to FIG. 11, there is shown a right side view (with FIG. 7 showing a left side view) of inspection unit 70. FIG. 12 shows a top view of inspection unit 70. With reference both figures, accelerometer 86 is shown mounted to the front end of first chassis half 74 along with lifting eyes 110, 112 and electrical connector 111. Lifting eyes 110, 112 are similar to lifting eye 98 and are mounted to the top portion of first chassis half 74 and are similarly used to facilitate the lifting and aligning of inspection system 70 during use. Electrical connector 111 is mounted to first chassis half 74 and is a multi-pin connector configured to electrically couple with a plug of a cable (not shown) to couple with first transducer 77, second transducer 85, and magnetic flux density sensors 99, 100 and connect with processing unit 4 (FIG. 1). Second transducer 85 is mounted to second magnetic flux leakage sensor assembly 120 which is mounted to first chassis half 74. Also shown in the figures are upper lug pair 113, 114 and lower lug pair 115, 116 which are configured to couple inspection unit 70 to rod support 80 either directly using support assemblies 82*a*, 82*b* or using a shock absorbing assembly as will be described in detail herein after with reference to FIG. 14.

Figure 13:
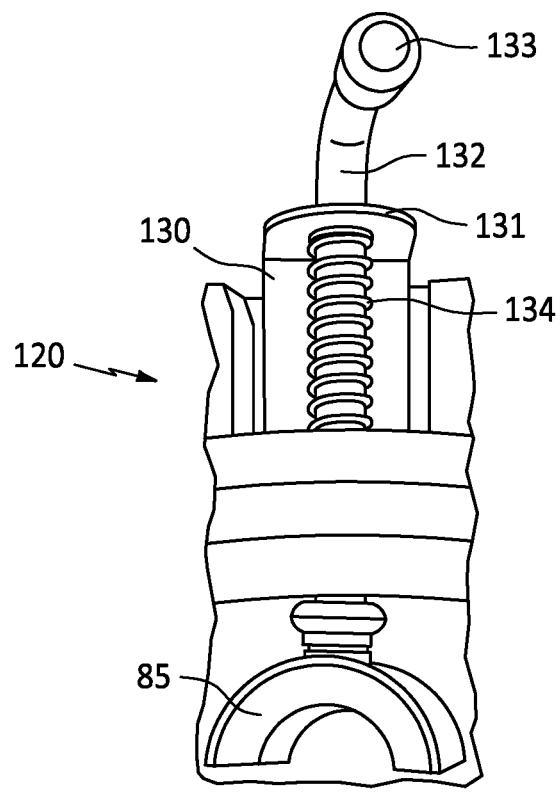
FIG. 13 is a front view of a magnetic flux leakage sensor assembly of a flaw detection system in accordance with the present disclosure.

Referring next to FIG. 13, there is shown magnetic flux leakage sensor assembly 120 which comprises transducer 85, mounting bracket 130 having shoulder 131, actuation rod 132 including handle portion 133 and biasing spring 134. Mounting bracket 130 is configured to be mounted to first chassis half. Actuation rod 132 is mechanically rotatably coupled to transducer 85 to allow the transducer to axially align with rod 5 (FIG. 1) during operation. Biasing spring 134 is captured between shoulder 131 and the bottom of actuation rod 132 such that it provides a downward biasing force on transducer 85 to maintain contact with rod 5 (FIG. 1) during operation. Handle 133 facilitates the lifting of rod 132 and transducer 85 thereby to allow the insertion of rod 5 during start up of an inspection procedure as will be disclosed in more detail herein after.

Figure 14:
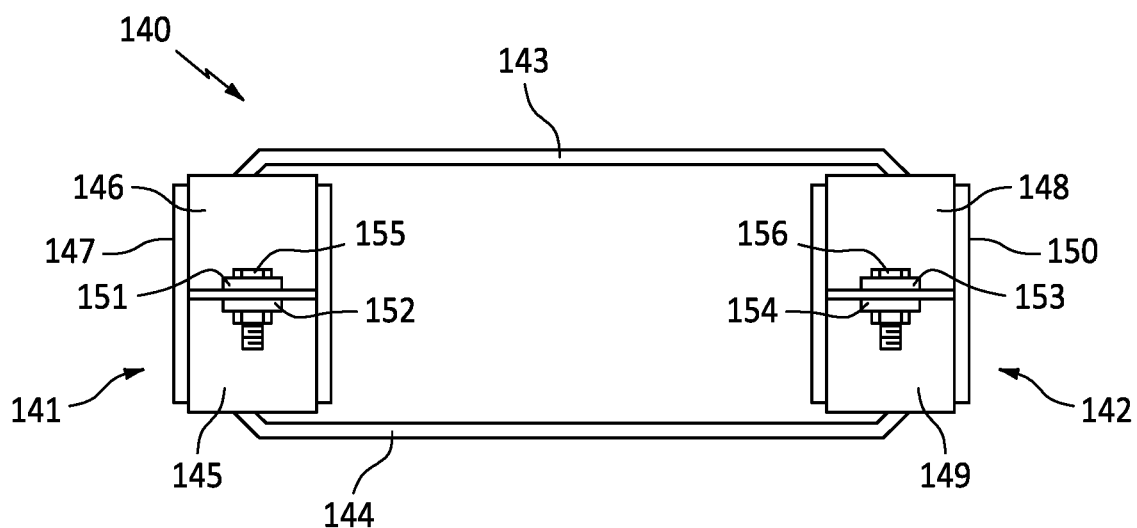
FIG. 14 is a side view of a shock absorbing assembly of an embodiment of a chassis of a flaw detection system in accordance with the present disclosure.

Shock absorbing assembly 140 is shown with reference to FIG. 14. Shock absorbing assembly 140 is comprised of first coupling end 141, second coupling end 142, upper tie bar 143 and lower tie bar 144. First coupling end 141 is comprised of upper outer sleeve 145 and a lower outer sleeve 146 and a hollow concentric compliant bushing 147. Similarly, second coupling end 142 is comprised of lower outer sleeve 148 and lower outer sleeve 149 and a hollow concentric compliant bushing 150. Upper outer sleeve 145, lower outer sleeve 146, upper outer sleeve 148 and lower outer sleeve 149, upper tie bar 143 and lower tie bar 144 can be comprised of any structurally suitable material such as metal. Upper tie bar 143 can be fixed to upper outer sleeves 145, 148 using any suitable method such as welding. Similarly, lower tie bar 144 can be fixed to lower outer sleeves 145, 149 using any suitable method such as welding. Upper outer sleeves include tabs 151, 152 respectively and lower outer sleeves 145, 149 include tabs 153, 154 respectively. Upper out sleeve 146 is rotatably attached to lower outer sleeve 145 by a hinge (not shown) opposite tabs 151, 152. Upper out sleeve 148 is rotatably attached to lower outer sleeve 149 by a hinge (not shown) opposite tabs 153, 154. Hollow concentric compliant bushings 147, 150 include a slit (not shown) and are sized to fit within upper outer sleeve 145 and a lower outer sleeve 146 and lower outer sleeve 148 and lower outer sleeve 149 and have an inner diameter sized to fit over the material to be inspected, such as rod 5 (FIG. 1).

In operation, hollow concentric compliant bushings 147, 150 are positioned over the piece to be inspected by opening the bushings at the slit. Upper outer sleeves 146, 148 and lower outer sleeves 145, 149 are installed over the hollow concentric compliant bushings. One end of shock absorbing assembly 140 is attached to upper lug pair 113, 114 and lower lug pair 115, 116 (FIGS. 11, 12) of inspection system 70 and the opposite end of the shock absorbing assembly is attached to rod support 80 (FIG. 7). The upper and lower halves of shock absorbing assembly 140 are joined by bolts 155, 156 which are tightened to provide a compression fit between hollow concentric compliant bushings 147, 150 and rod 5. It should be appreciated by those skilled in the art that shock absorbing assembly 140 functions to dampen energy spikes from the rod as it approaches and moves through the inspection system.

With reference back to FIGS. 7-14, the operation of Inspection system 70 can be disclosed. Rod 5 is positioned within rod support 80 and may be attached to a drive unit (such as drive unit 66 in FIG. 6). Shock absorbing assembly 140 is positioned as disclosed immediately herein above. First chassis half 74 is placed over rod 5 with transducer 85 in contact with the rod. Second chassis half 75 is mated to first chassis half 74 with alignment pins 103, 104,105, 106 mating alignment bores 93, 94, 95, 96 respectively and the chassis halves are fastened together the rod positioned within the full bore created by first channel 92 and second channel 102 with first transducer in contact with the rod and V-groove wheel 78 positioned over the rod such that the rod is slidable engaged within inspection system 70. Shock absorbing assembly 140 is then attached to support assembly 82 and inspection system 70. Electrical cables are electrically coupled to electrical connector 111. Once assembled as disclosed, wireless energizing unit 2 produces a magnetic field in rod 5 both in a direction transverse to its centerline 8 as well as linearly along its centerline. In operation, rod 5 is translated in direction 84 while inspection system 70 remains stationary. At least one of the plurality of transducers 77, 85 is configured to detect a magnetic flux leak if a flaw 51 (FIG. 5) is present within rod 5 as it is translated in direction 84. Magnetic flux density sensors are configured to sense and report the magnetic flux density produced by the wireless energizing unit 2. Once rod 5, or other object, has been inspected the assembly procedure for inspection system 70 is reversed and it is removed from the rod.

Figure 15:
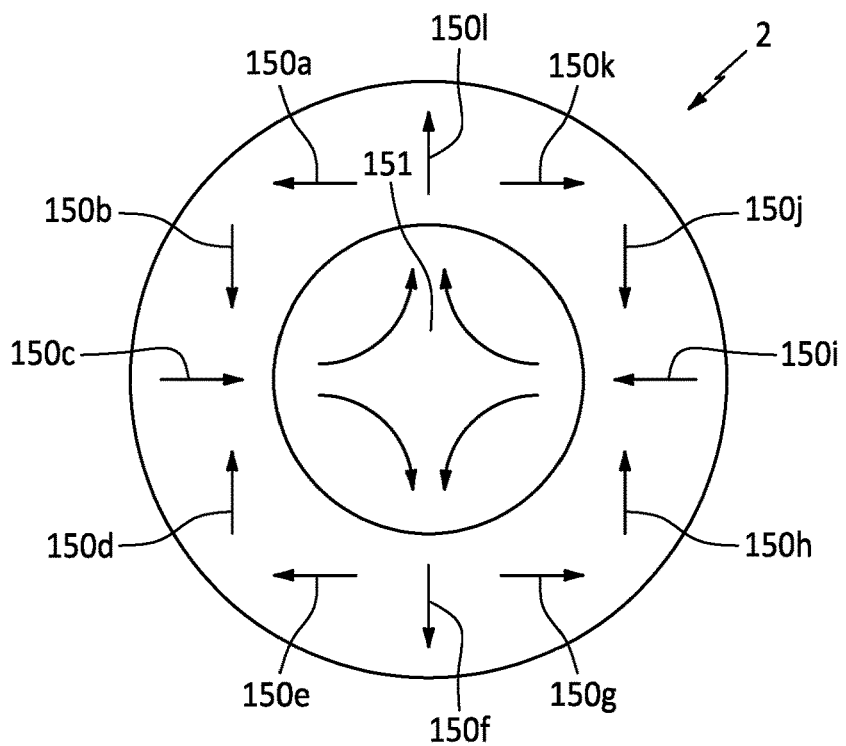
FIG. 15 is a diagrammatic view of the combined magnetic field in accordance with the present disclosure.
Figure 16:
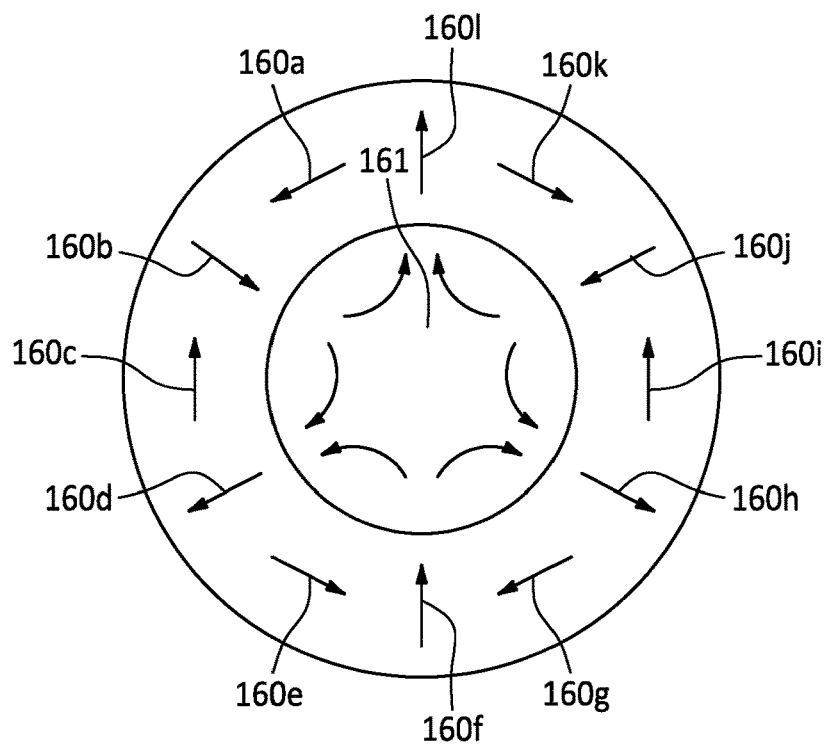
FIG. 16 is a diagrammatic view of the combined magnetic field in accordance with the present disclosure.

Other embodiments of wireless energizing unit 2 of the present disclosure can best be seen by reference to FIGS. 15, 16. With regard to FIG. 15, there is shown an embodiment of wireless energizing unit 2 including magnets 150$a$-150$l$ arranged evenly spaced around midpoint circumference of the ring between its inside diameter and outside diameter. The magnets 150$a$-150$l$ can comprise any type of permanent magnet or electromagnetic magnets and can comprise rare earth magnets. The direction of the magnetic field for each of the magnets 150$a$-150$l$ is indicated by the arrow for each of the respective magnets. Although the embodiment in FIG. 15 comprises 12 magnets 150$a$-150$l$, embodiments with more or fewer magnets are contemplated to be within the scope of the present disclosure. In the embodiment shown, magnets 150$a$-150$l$ produce a combined magnetic field in the plane of ring 2 and in the direction of arrows 151. It should be appreciated by those skilled in the art that wireless energizing unit 2 resembles a Halbach array of the type k=3.

Referring next to FIG. 16, there is shown an embodiment of wireless energizing unit 2 including magnets 160$a$-160$l$ arranged evenly spaced around midpoint circumference of the ring between its inside diameter and outside diameter. The magnets 160$a$-160$l$ can comprise any type of permanent magnet or electromagnetic magnets and can comprise rare earth magnets. The direction of the magnetic field for each of the magnets 160$a$-160$l$ is indicated by the arrow for each of the respective magnets. Although the embodiment in FIG. 16 comprises 12 magnets 160$a$-160$l$, embodiments with more or fewer magnets are contemplated to be within the scope of the present disclosure. In the embodiment shown, magnets 160$a$-160$l$ produce a combined magnetic field in the plane of ring 2 and in the direction of arrows 161. It should be appreciated by those skilled in the art that wireless energizing unit 2 resembles a Halbach array of the type k=4 in which all the flux is confined to the center of the bore.

In other embodiments of the present disclosure inspection system 70 can be translated relative to the object to be inspected. In an example embodiment for inspecting a cable fastened between two trusses (not shown), wireless energizing unit 2 can be assembled as disclosed immediately herein above over the cable. V-groove wheels 78, 79 can be positioned such that the cable is positioned within the full bore of first chassis half 74 and second chassis half 75 and in the center of wireless energizing unit 2. Inspection system 70 can then be translated along the cable to inspect for flaws in the manner disclosed herein above for rods and other objects comprised of ferromagnetic material.

It should be appreciated by those skilled in the art that wireless energizing unit 2 can be used to replace the aforementioned powered magnetizing coils in EMI inspection units of the prior art. Such prior art EMI inspection units can be retrofitted with wireless energizing unit 2 by simply designing the wireless energizing unit to substantially match the magnetic field produced by the powered magnetizing coils. Such a retrofitted EMI inspection unit would gain all the improvements of wireless energizing unit 2 disclosed herein and provide heretofore unrealized gains in the field of rod and pipe EMI inspection capability.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements.

While the foregoing is directed to embodiments of the present disclosure, other and further embodiments of the disclosure may be devised without departing from the basic scope thereof, and the scope thereof is determined by the claims that follow.

What is claimed is:

1. A magnetic inspection system, comprising:
    a sensor unit comprising:
        at least one wireless energizing unit configured to produce a planar magnetic field in a part of interest comprising:
            a ring having an inside diameter and an outside diameter and a bore defined by the inside diameter; and
            a plurality of permanent magnets circumferentially spaced around the ring between the inside diameter and the outside diameter wherein each of the plurality of permanent magnets is oriented such that the magnetic field of each of the permanent magnets is directed in a predetermined direction;
        a first chassis half and a second chassis half, wherein the ring is comprised of a first ring portion and a second ring portion, and wherein the first ring portion is fixedly attached to the first chassis half and the second ring portion is fixedly attached to the second chassis half and wherein the first chassis half and the second chassis half are positioned over the part of interest and removably coupled together joining the first ring portion and the second ring portion slidably capturing the part of interest in the bore formed therebetween;
        wherein the part of interest includes a centerline and is at least in part comprised of a ferromagnetic material;
        wherein each of the at least one wireless energizing unit is positioned at a predetermined angle relative to the centerline of the part of interest;
    at least one transducer configured to detect a magnetic parameter in the part of interest a magnetic parameter signal; and
    a processing unit configured to process the magnetic parameter signal and to output information related to the magnetic parameter.

2. The magnetic inspection system of claim 1 wherein the predetermined angle is between substantially 1 degree and 90 degrees relative to the centerline of the part of interest.

3. The magnetic inspection system of claim 2 wherein the plurality of permanent magnets circumferentially spaced around the ring comprise a Halbach array having a magnetization pattern of any of k=2, k=3 and k=4.

4. The magnetic inspection system of claim 3 wherein the Halbach array is of a type k=2 and the planar magnetic field is in accordance with the following:

$$H = M_r[\ln(\text{[...]})\frac{R_o}{R_i}]y$$

wherein $M_r$ is a ferromagnetic remanence, $R_i$ is an inside radius of the ring and $R_o$ is an outside radius of the ring and a direction of the planar magnetic field is y.

5. The magnetic inspection system of claim 2 wherein the magnetic parameter is any of a magnetic flux, a magnetic flux density and a magnetic flux leakage.

6. The magnetic inspection system of claim 5 wherein the magnetic parameter comprises the magnetic flux leakage and is used to determine a flaw in the part of interest and the magnetic parameter signal is a flaw detection signal.

7. The magnetic inspection system of claim 6 wherein the at least one wireless energizing unit comprises a first wireless energizing unit and a second wireless energizing unit.

8. The magnetic inspection system of claim 7 wherein the first wireless energizing unit is configured to produce the planar magnetic field in a first planar magnetic field direction and the second wireless energizing unit is configured to produce the planar magnetic field in a second planar magnetic field direction.

9. The magnetic inspection system of claim 8 wherein the first planar magnetic field direction is substantially equal to the second planar magnetic field direction.

10. The magnetic inspection system of claim 8 wherein the first planar magnetic field direction is substantially different from the second planar magnetic field direction.

11. The magnetic inspection system of claim 8 wherein the first wireless energizing unit and the second wireless energizing unit are configured to rotate independently of one another.

12. The magnetic inspection system of claim 2 wherein:
    the part of interest comprises a circular cross section, a linear length and a centerline through the circular cross section along the linear length; and
    the part of interest is configured to be positioned within the bore and the ring of the at least one wireless energizing unit is configured to be positioned at a predetermined angle to the centerline and configured to induce the planar magnetic field in the part of interest with the direction of the planar magnetic field along at least a portion of the linear length.

13. The magnetic inspection system of claim 12 wherein the at least one wireless energizing unit is configured to be positioned at different locations along the linear length of the part of interest.

14. The magnetic inspection system of claim 13 wherein the ring is configured to rotate about the centerline.

15. The magnetic inspection system of claim 6 further comprising a linear measurement device and wherein the magnetic inspection system is configured to permit the part of interest to be translated along a linear length of the part of interest.

16. The magnetic inspection system of claim 15 wherein the linear measurement device is configured to indicate a position of the flaw along the linear length of the part of interest when the at least one transducer detects the magnetic flux leakage.

17. The magnetic inspection system of claim 16 further comprising a first V-groove wheel rotatably fixedly attached to the first chassis half and a second V-groove wheel rotatably fixedly attached to the second chassis half and configured to engage with the part of interest and position the part of interest proximate the center of the bore of the ring.

18. The magnetic inspection system of claim 17 wherein the ring, the first chassis half, and the second chassis half are comprised of a non-ferromagnetic material.

19. The magnetic inspection system of claim 17 wherein the first V-groove wheel and the second V-groove wheel are comprised of a non-ferromagnetic material.

20. A method of inspecting a ferromagnetic part of interest, comprising:
producing at least one planar magnetic field in the part of interest using at least one wireless energizing unit wherein the at least one wireless energizing unit comprises:
a ring having an inside diameter and an outside diameter and a bore defined by the inside diameter; and
a plurality of permanent magnets circumferentially spaced around the ring between the inside diameter and the outside diameter wherein each of the plurality of permanent magnets is oriented such that the magnetic field of each of the permanent magnets is directed in a predetermined direction;
wherein the ring is comprised of a first ring portion and a second ring portion;
positioning the first ring portion and the second ring portion over the part of interest;
attaching the first ring portion to a first chassis half;
attaching the second ring portion to a second chassis half;
coupling the first chassis half and the second chassis together; and
slidably capturing the part of interest in the bore formed by the first ring portion and the second ring portion;
positioning of the at least one wireless energizing unit at a predetermined angle relative to a centerline of the part of interest;
detecting a magnetic parameter using at least one transducer;
producing a magnetic parameter signal; and
outputting information related to the magnetic parameter using a processing unit.

21. The method of inspecting a ferromagnetic part of interest of claim 20 wherein the predetermined angle is between substantially 1 degree and 90 degrees relative to the centerline of the part of interest.

22. The method of inspecting a ferromagnetic part of interest of claim 21 wherein the plurality of permanent magnets circumferentially spaced around the ring comprise a Halbach array having a magnetization pattern of any of k=2, k=3 and k=4.

23. The method of inspecting a ferromagnetic part of interest of claim 22 wherein the Halbach array is of a type k=2 and producing the planar magnetic field is in accordance with the following:

$$H = M_r [\ln(\dots)] \frac{R_o}{R_i} \hat{y}$$

wherein $M_r$ is a ferromagnetic remanence, $R_i$ is an inside radius of the ring and $R_o$ is an outside radius of the ring and a direction of the planar magnetic field is y.

24. The method of inspecting a ferromagnetic part of interest of claim 22 wherein the detecting the magnetic parameter is any of detecting a magnetic flux, detecting a magnetic flux density and detecting a magnetic flux leakage.

25. The method of inspecting a ferromagnetic part of interest of claim 24 further comprising determining a flaw in the part of interest using the magnetic flux leakage and producing a flaw detection signal.

26. The method of inspecting a ferromagnetic part of interest of claim 25 wherein the at least one wireless energizing unit comprises a first wireless energizing unit and a second wireless energizing unit.

27. The method of inspecting a ferromagnetic part of interest of claim 26 further comprising:
producing the planar magnetic field in a first planar magnetic field direction using the first wireless energizing unit; and
producing the planar magnetic field in a second planar magnetic field direction using the second wireless energizing unit.

28. The method of inspecting a ferromagnetic part of interest of claim 27 wherein the first planar magnetic field direction is substantially equal to the second planar magnetic field direction.

29. The method of inspecting a ferromagnetic part of interest of claim 27 wherein the first planar magnetic field direction is substantially different from the second planar magnetic field direction.

30. The method of inspecting a ferromagnetic part of interest of claim 27 further comprising rotating the first wireless energizing unit about the part of interest and rotating the second wireless energizing unit about the part of interest.

31. The method of inspecting a ferromagnetic part of interest of claim 21
wherein: the part of interest comprises a circular cross section, a linear length and a centerline through the circular cross section along the linear length; and
the method further comprising:
positioning the at least one wireless energizing unit at a predetermined angle to the part of interest comprises positioning the at least one wireless energizing unit at a predetermined angle to at a predetermined angle to the centerline; and
producing at least one planar magnetic field in the part of interest comprises producing the planar magnetic field in the part of interest with the direction of the planar magnetic field along at least a portion of the linear length.

32. The method of inspecting a ferromagnetic part of interest of claim 31 further comprises positioning the at least one wireless energizing unit at different locations along the linear length of the part of interest.

33. The method of inspecting a ferromagnetic part of interest of claim 32 further comprising rotating the ring about the centerline.

34. The method of inspecting a ferromagnetic part of interest of claim 20 further comprising translating the part of interest along a linear length and measuring a linear distance of translation.

35. The method of inspecting a ferromagnetic part of interest of claim 34 further comprising indicating a position of the flaw along the linear length of the part of interest when the flaw detection signal is produced.

36. The method of inspecting a ferromagnetic part of interest of claim 35 further comprising centering the part of interest in the bore of the ring.

37. The method of inspecting a ferromagnetic part of interest of claim 36 further comprising selecting a non-ferromagnetic material to comprise the ring, the first chassis half and the second chassis half.

* * * * *